(12) United States Patent
Miles (10) Patent No.: US 11,602,574 B1
(45) Date of Patent: Mar. 14, 2023

(54) ULTRAVIOLET DISINFECTING AND IDENTIFICATION SYSTEM

(71) Applicant: Stanley Kevin Miles, Foresthill, CA (US)

(72) Inventor: Stanley Kevin Miles, Foresthill, CA (US)

(*) Notice: Subject to any disclaimer, the term of this patent is extended or adjusted under 35 U.S.C. 154(b) by 270 days.

(21) Appl. No.: 17/013,442

(22) Filed: Sep. 4, 2020

(51) Int. Cl.
| | | |
|---|---|---|
| A61L 2/24 | (2006.01) | |
| G01B 21/20 | (2006.01) | |
| G06K 7/14 | (2006.01) | |
| A61L 2/10 | (2006.01) | |

(52) U.S. Cl.
CPC ............ *A61L 2/24* (2013.01); *A61L 2/10* (2013.01); *G01B 21/20* (2013.01); *G06K 7/1417* (2013.01); *A61L 2202/11* (2013.01); *A61L 2202/14* (2013.01)

(58) Field of Classification Search
CPC .......... A61L 2/24; A61L 2/10; A61L 2202/11; A61L 2202/14; G01B 21/20; G06K 7/1417
See application file for complete search history.

(56) References Cited

U.S. PATENT DOCUMENTS

| | | | | |
|---|---|---|---|---|
| 5,526,119 A | * | 6/1996 | Blit ........................ | B07C 5/3422 356/402 |
| 6,373,520 B1 | * | 4/2002 | Cadieux, Jr. ............ | B65B 19/28 348/125 |
| 10,984,378 B1 | * | 4/2021 | Eckman ........... | G06K 19/06131 |
| 2007/0160373 A1 | * | 7/2007 | Biegelsen ............ | H05B 47/195 398/118 |
| 2012/0209741 A1 | * | 8/2012 | Bonner .................. | G06Q 30/08 705/26.3 |

\* cited by examiner

*Primary Examiner* — Regina M Yoo
(74) *Attorney, Agent, or Firm* — Perkins Coie LLP (57) ABSTRACT

An item or object is exposed to electromagnetic light using a plurality of electromagnetic light emitters that are arranged throughout an enclosed structure. A plurality of images of the item or object is captured by a plurality of image sensors that are arranged throughout the enclosed structure. A first pattern in at least one image is recognized. The first pattern includes encoded information associated with the item and the first pattern is visible in response to the exposure of the item to the electromagnetic light. The encoded information is decoded and the item is identified based on the decoded information.

19 Claims, 6 Drawing Sheets

ULTRAVIOLET DISINFECTING AND IDENTIFICATION SYSTEM

FIELD OF THE INVENTION

The invention relates to disinfecting an item or object using a plurality of ultraviolet (UV) light emitters and identifying an item that is exposed to the UV light radiated by the plurality of UV light emitters.

SUMMARY OF THE INVENTION

Aspects of the invention relate to methods, apparatuses, and/or systems for disinfecting an item using a plurality of UV light emitters and identifying an item based on its exposure to the UV light radiated by the UV light emitters.

An aspect of the disclosure relates to a system and/or method for disinfecting and identifying an item. In some embodiments, a plurality of ultraviolet (UV) light emitters may be arranged in a tunnel structure and may be configured to expose an item to UV light. Further, in some embodiments, a plurality of cameras may also be arranged in the tunnel structure and may be configured to capture a plurality of images of the item exposed to the UV light. The cameras may be arranged between the UV light emitters. In some embodiments, a first pattern in at least one image may be recognized from the plurality of images. The first pattern may include encoded information associated with the item. In some embodiments, the first pattern may be visible in response to the exposure of the item to the UV light, while in other embodiments, the first pattern may be visible regardless of UV light. Further, the encoded information may be decoded, for example, using a decoding algorithm and the item may be identified based on the decoded information.

Various other aspects, features, and advantages of the invention will be apparent through the detailed description of the invention and the drawings attached hereto. It is also to be understood that both the foregoing general description and the following detailed description are examples and not restrictive of the scope of the invention. As used in the specification and in the claims, the singular forms of "a," "an," and "the" include plural referents unless the context clearly dictates otherwise. In addition, as used in the specification and the claims, the term "or" means "and/or" unless the context clearly dictates otherwise.

DETAILED DESCRIPTION OF THE INVENTION

In the following description, for the purposes of explanation, numerous specific details are set forth in order to provide a thorough understanding of the embodiments of the invention. It will be appreciated, however, by those having skill in the art that the embodiments of the invention may be practiced without these specific details or with an equivalent arrangement. In other cases, well-known structures and devices are shown in block diagram form in order to avoid unnecessarily obscuring the embodiments of the invention.

Figure 1:
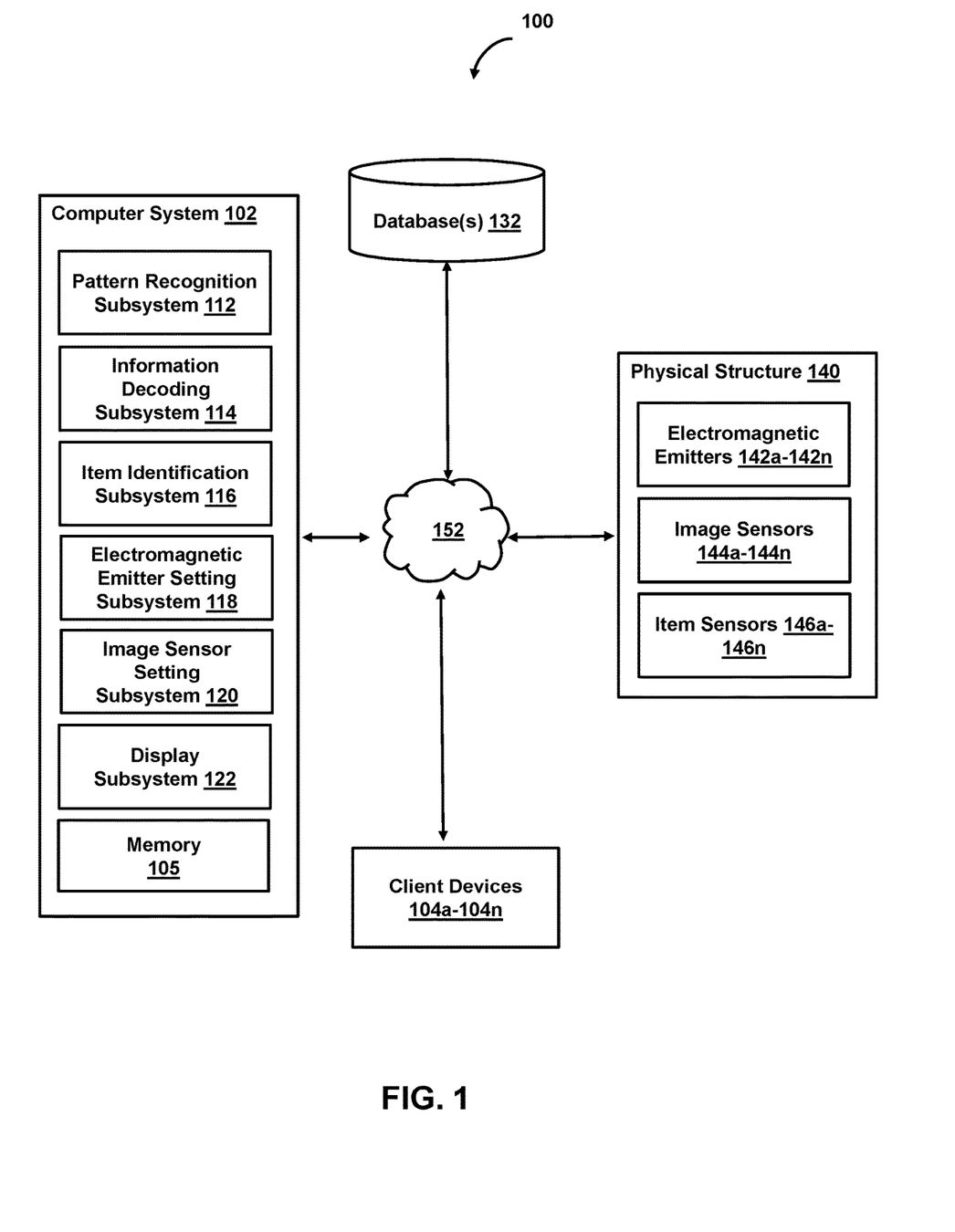
FIG. 1 shows an UV disinfection and identification system, in accordance with one or more embodiments.

FIG. 1 shows an ultraviolet system 100 for disinfecting and identifying an item, in accordance with one or more embodiments. In some embodiments, the system may include a tunnel structure that includes a first opening (e.g., via which an item enters the tunnel structure) and a second opening (e.g., via which the item exits the tunnel structure). The system may further include a plurality of UV light emitters that are configured to expose an item to UV light. The plurality of UV light emitters may be arranged throughout the tunnel structure such that a first UV light emitter is arranged at a first location proximate the first opening and a second UV light emitter is arranged at a second location proximate the second opening. In addition, the system may include a plurality of cameras that are configured to capture a plurality of images of the item exposed to the UV light. In some embodiments, the plurality of cameras may be arranged throughout the tunnel structure in between the plurality of UV light emitters such that at least one camera is arranged between the first location and the second location of the tunnel structure. Based on the plurality of images, the system may recognize a first pattern associated with the item. The first pattern may include encoded information associated with the item. The system may decode the encoded information and may identify the item based on the decoded information. In some embodiments, the first pattern may be visible in response to the exposure of the item to the UV light and in other embodiments the first pattern may be visible regardless of the exposure of the item to the UV light or any other electromagnetic light.

As shown in FIG. 1, system 100 may include computer system 102 (e.g., one or more servers, circuitry, one or more processors), client device 104 (or client devices 104a-104n), physical structure 140, database 132, or other components. Computer system 102 may include a pattern recognition subsystem 112, information decoding subsystem 114, item identification subsystem 116, electromagnetic emitter setting subsystem 118, image sensor setting subsystem 120, display subsystem 122, memory 105, or other components. Client device 104 (also referred to as a physical device or a user device) may include any type of mobile terminal, fixed terminal, or other device. By way of example, client device 104 may include a desktop computer, a notebook computer, a tablet computer, a smartphone, a wearable device (e.g., a VR/AR headset, eye wear, or other wearable device), or other physical client device. In some embodiments, the computer system 102 may correspond to a client device 104. The physical structure 140 (e.g., an ultraviolet (UV) tunnel structure) may include an electromagnetic emitter 142 (or electromagnetic emitters 142a-142n, or electromagnetic light emitter 142) (e.g., UV light emitters, UV lamps), an image sensor 144 (or image sensors 144a-144n) (e.g., cameras, optical readers), and an item sensor 146 (or item sensors 146a-146n, or object sensors, or object detectors) (e.g., electromechanical sensors, pneumatic sensors, magnetic sensors, inductive sensors, capacitive sensors, photoelectric sensors, ultrasonic sensors, displacement sensors, or measurement sensors). In some embodiments, the computer system 102, client device 104, physical structure 140, and database 132 may be physically co-located and may be physically or wirelessly connected to each other. In some embodiments, the computer system 102 and/or client device 104 may be wirelessly or physically connected to the physical structure 140.

Users may, for instance, utilize one or more client devices 104 to interact with one another, one or more computer systems 102, or other components of system 100. It should be noted that, while one or more operations are described herein as being performed by components of computer system 102, those operations may, in some embodiments, be performed by components of client device 104 or other components of system 100 and while one or more operations are described herein as being performed by components of client device 104, those operations may, in some embodiments, be performed by components of computer system 102 or other components of system 100.

Figure 2A:
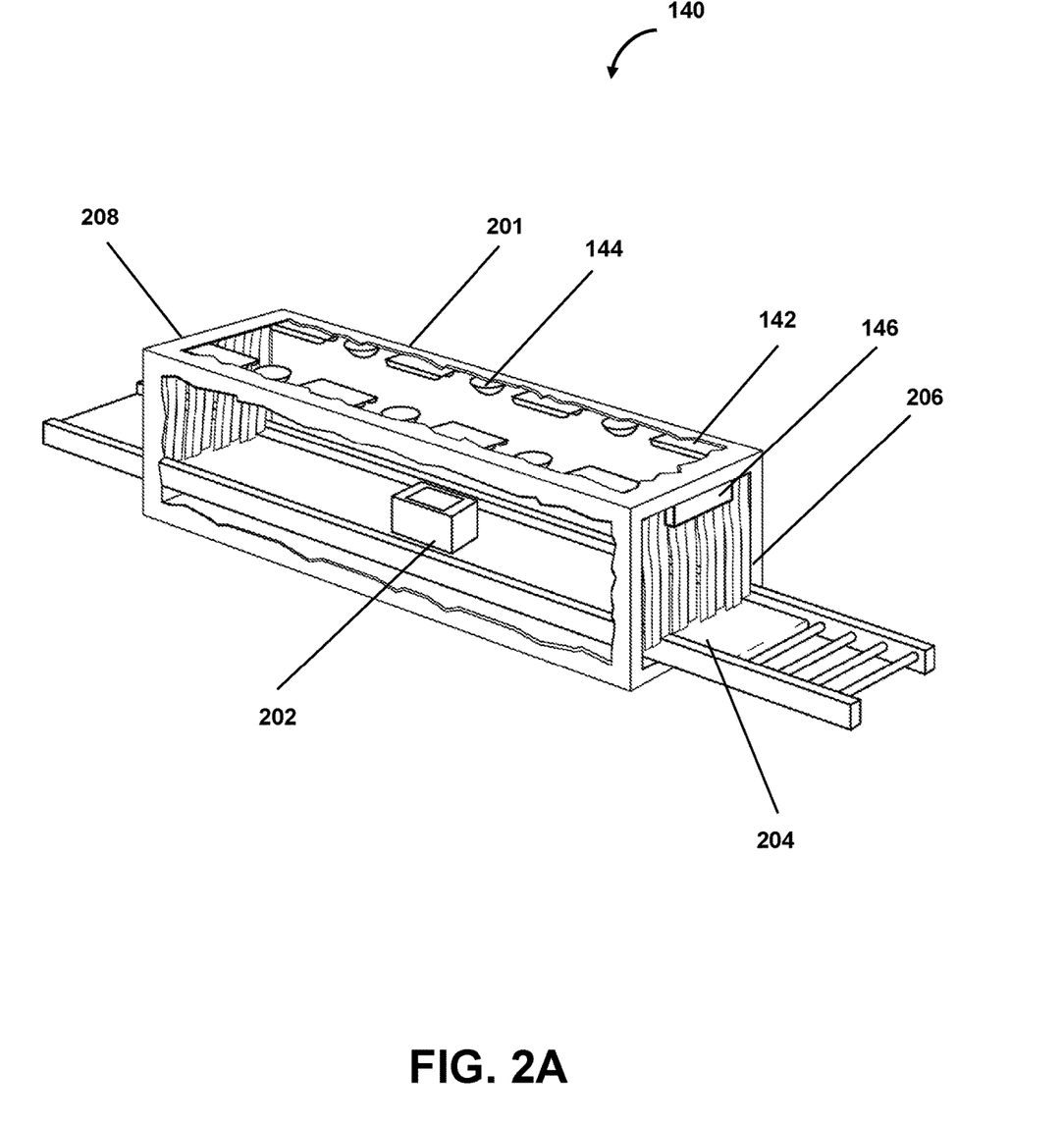
FIG. 2A shows a UV tunnel structure, in accordance with one or more embodiments.
Figure 2B:
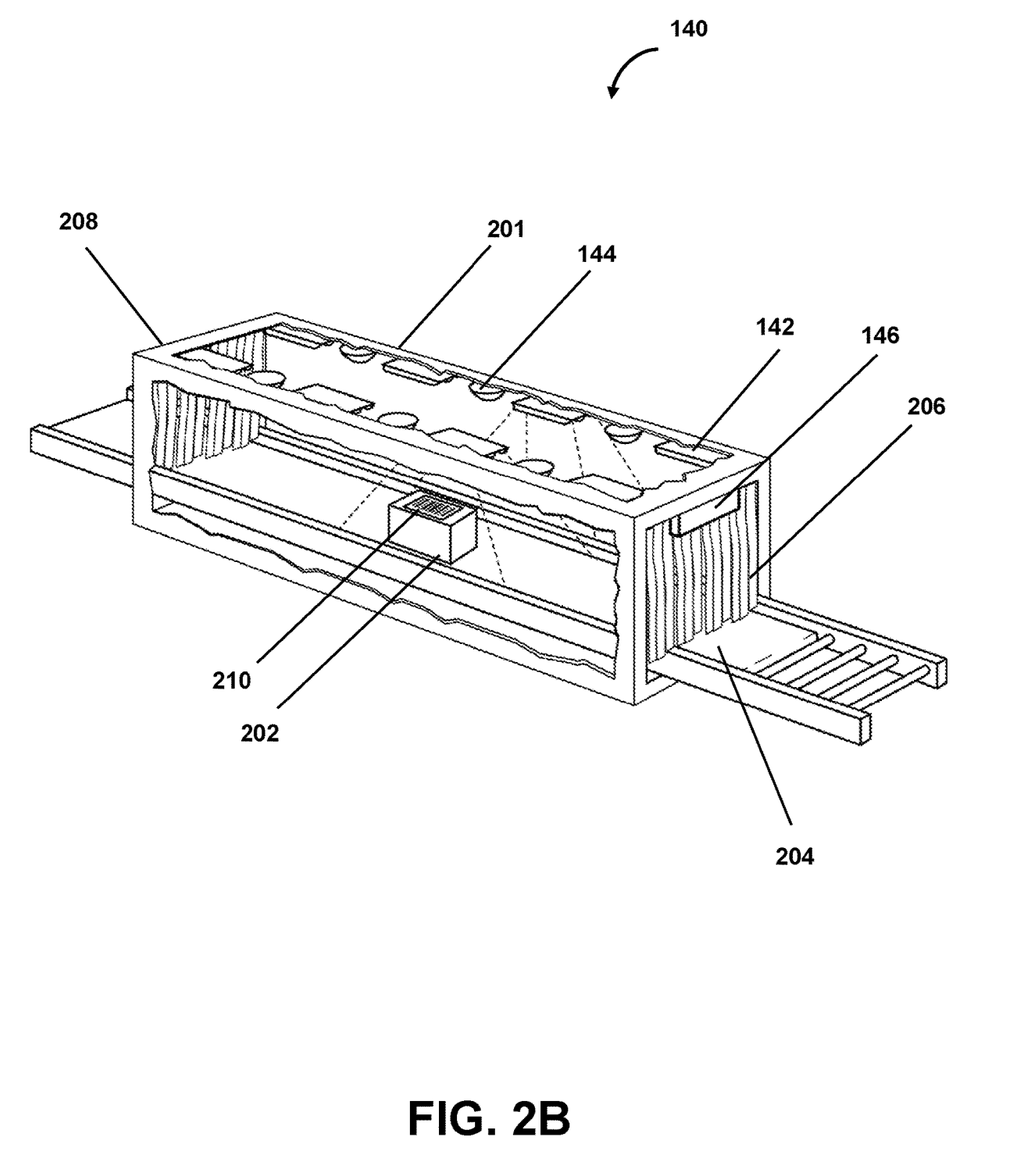
FIG. 2B shows a UV tunnel structure, in accordance with one or more embodiments.

In some embodiments, the physical structure 140 may include an enclosed structure 201 (e.g., a UV disinfecting and sanitizing tunnel structure) through which one or more items (or objects) may be transported using a belt, thereby allowing the electromagnetic emitters 142 (e.g., the UV emitters) to help sanitize and disinfect the one or more items (or objects). Although 201 is referred to an enclosed structure, certain portions of the enclosed structure 201 may not be completely enclosed and the enclosed structure 201 may have one or more openings. In some embodiments, an item 202 may be placed on a belt 204 (see FIGS. 2A and 2B) and the belt 204 may be configured to move in a specific direction. As illustrated in FIGS. 2A and 2B, the enclosed structure 201 may include a first opening 206 via which an item 202 may enter the enclosed structure 201 (e.g., the item 202 may be placed on the belt 204 and the item 202 may enter the enclosed structure 201 when the belt 204 moves in a specific direction) and a second opening 208 via which the item 202 exits the enclosed structure 201. The enclosed structure 201 may include a plurality of electromagnetic emitters 142 placed within the enclosed structure 201. For example, the plurality of electromagnetic emitters 142 may be placed above the belt 204, below the belt 204, and/or parallel to the belt 204 within the enclosed structure 201 such that the item 202 (or object) is sanitized or disinfected from all directions. In other words, the plurality of electromagnetic emitters 142 may be placed or arranged at different positions within or throughout the enclosed structure 201 (e.g., one or more first electromagnetic emitters 142a may be arranged at a first location proximate the first opening 206 and one or more second electromagnetic emitters 142b may be arranged at a second location proximate the second opening 208).

In addition to the electromagnetic emitters 142, in some embodiments, one or more image sensors 144 (e.g., cameras, optical readers) may be arranged throughout the enclosed structure 201. As shown in FIGS. 2A and 2B, one or more image sensors 144 may be interspersed between the plurality of electromagnetic emitters 142 within the enclosed structure 201. For example, at least one image sensor 144 may be arranged between a first electromagnetic emitter 142a and a second electromagnetic emitter 142b. In some embodiments, one or more electromagnetic emitters 142 may be interspersed between a plurality of image sensors 144 within the enclosed structure 201. Further, in some embodiments, the enclosed structure 201 may include one or more item sensors 146, which may be arranged throughout the enclosed structure 201, including at or proximate the first opening 206 and/or second opening 208.

In some embodiments, an item may be placed on the belt 204 and the belt 204 may be set in motion such that the item 202 (or a plurality of items 202) enters the enclosed structure 201 via the first opening 206. In some embodiments, the item sensor 146 may detect the item 202 and notify the computer system 102 of detected item 202. In some embodiments, the item sensor 146 may be configured to detect a size of the item 202 and notify the computer system 102 of the size of the item 202. In response to the obtaining a notification from the item sensor 146 that an item 202 has been detected, the computer system 102 (e.g., electromagnetic emitter setting subsystem 118) may generate a signal to turn on one or more of the electromagnetic emitters 142. For example, the computer system 102 (e.g., electromagnetic emitter setting subsystem 118) may generate a signal to turn on (e.g., a first state) one or more electromagnetic emitters 142 that are proximate to the location (or position) of the item 202 on the belt 204, while the other electromagnetic emitters 142 remain off (e.g., a second state). In other words, based on a detected location (or position) of the item 202 (e.g., detected by one or more item sensors 146, which may be arranged throughout the enclosed structure 201) within the enclosed structure 201, the computer system 102 may turn on certain electromagnetic emitters 142 (such that certain electromagnetic emitters 142 emit electromagnetic radiation) that are proximate to the item 202, while maintaining the other electromagnetic emitters 142 in an off state. This is advantageous because it reduces the amount of power required to maintain the electromagnetic emitters 142 in an on state. In some embodiments, once the item 202 moves away from the electromagnetic emitters 142 that were turned on, the computer system 102 (e.g., electromagnetic emitter setting subsystem 118) may generate a signal to turn off such electromagnetic emitters 142 in response to a change in the location of the item 202 (e.g., in response to the item 202 being more than a threshold distance from such electromagnetic emitters 142). In some embodiments, the electromagnetic emitters 142 may automatically turn off a threshold period of time after they were turned on. The threshold period of time may be dependent on, for example, an amount of power consumed by the physical structure 140, total amount of power consumed by an infrastructure (not shown) that houses the physical structure 140, and/or the time during the day. Alternatively, in response to a detection of an item 202 by the item sensor 146, the computer system 102 may generate a signal to turn on all of the electromagnetic emitters 142 within the enclosed structure 201. When no item is detected, the electromagnetic emitters 142 may remain in an off state.

In some embodiments, the computer system 102 may determine a set of electromagnetic emitters 142 to turn on. Such a set may include every second electromagnetic emitter 142, every third electromagnetic emitter 142, etc. Such a determination of a set of electromagnetic emitters 142 may be based on one or more factors, including, for example, a size of the detected item, amount of power consumed by the physical structure 140, total amount of power consumed by an infrastructure (not shown) that houses the physical structure 140, and/or the time during the day. For example, the computer system 102 may determine or obtain a value of the amount of power consumed by the physical structure 140 (e.g., via an electrical usage monitor) and based on the value of the amount of power consumed by the physical structure 140, the computer system 102 (e.g., electromagnetic emitter setting subsystem 118) may determine a number of electromagnetic emitters 142 to turn on in order to disinfect and sanitize a particular item. In some embodiments, the determination of the number of electromagnetic emitters 142 to turn on (e.g., in response to a detection of an item) may be a multi-tiered determination. For example, if a value of the amount of power consumed by the physical structure 140 is above a first threshold, then the computer system 102 may determine a first number of electromagnetic emitters 142 to turn on and if a value of the amount of power consumed by the physical structure 140 is above a second threshold, then the computer system 102 may determine a second number of electromagnetic emitters 142 to turn on. Similar determinations may be made by the computer system 102 based on the obtained or determined value of an amount of power consumed by an infrastructure (not shown) that houses the physical structure 140.

Figure 3:
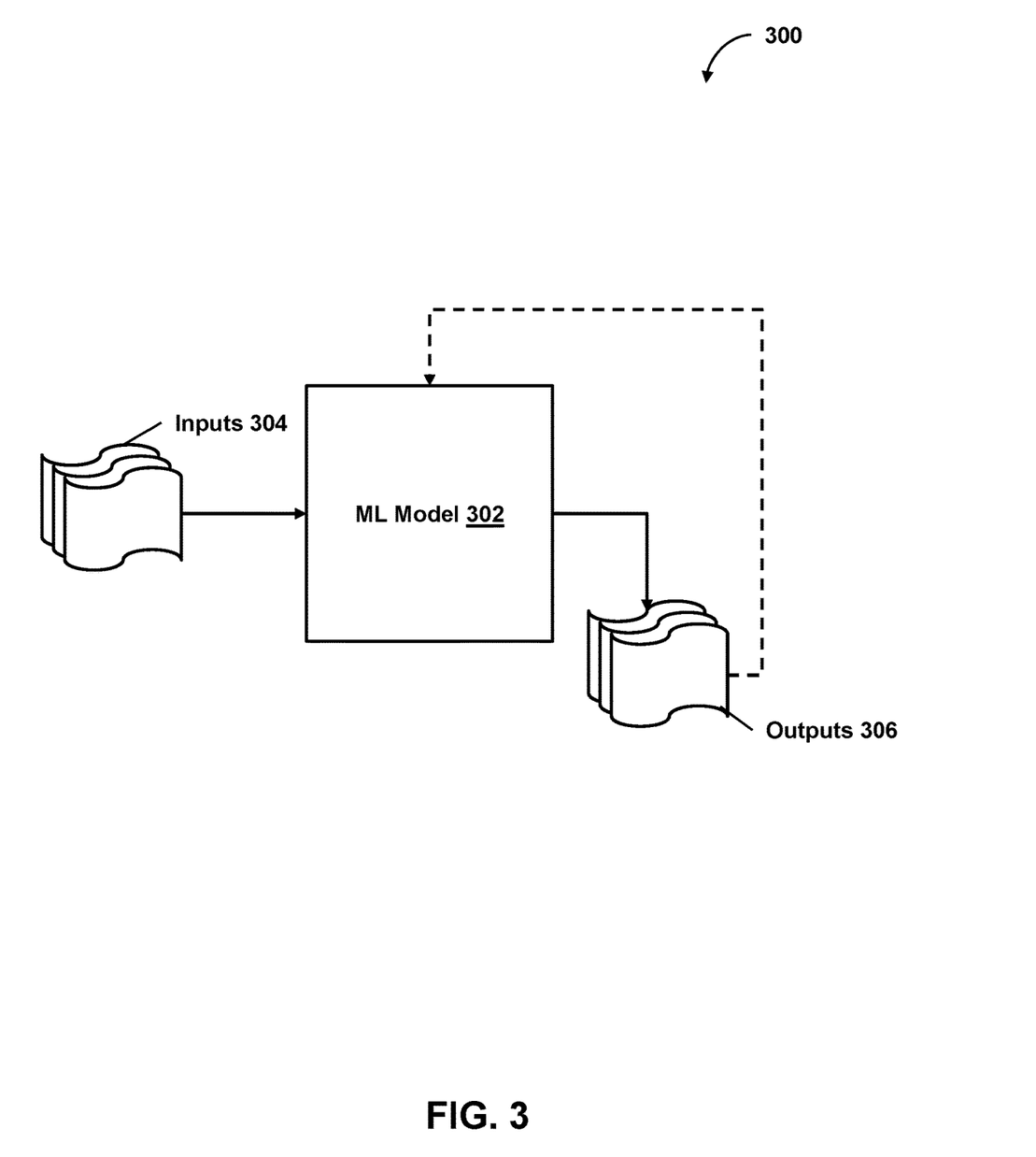
FIG. 3 shows a machine learning model system for predicting an amount of power consumed at different times during the day, in accordance with one or more embodiments.

In some embodiments, the computer system 102 may determine or predict an amount of power consumed at different times during the day and based on such a determination or prediction, may determine a number of electromagnetic emitters 142 to turn on. For example, the computer system 102 may determine that at 1 pm, the consumption of power is at 50% and at 3 pm, the consumption of power is at 85%. The computer system 102 may determine a number of electromagnetic emitters 142 to turn on based on a current time and based on such determinations of the consumption of power at different times during the day. In some embodiments, computer system 102 may utilize a machine learning model to facilitate the prediction of an amount of power consumed at a specific time during the day. FIG. 3 illustrates a machine learning model system 300 for predicting an amount of power consumed at different times during the day. As an example, a machine learning model 302 may take inputs 304 and provide outputs 306. In one use case, outputs 306 may be fed back (e.g., active feedback) to machine learning model 302 as input to train machine learning model 302 (e.g., alone or in conjunction with user indications of the accuracy of outputs 306, labels associated with the inputs 304, or with other reference feedback information). In another use case, machine learning model 302 may update its configurations (e.g., weights, biases, or other parameters) based on its assessment of its prediction (e.g., outputs 306) and reference feedback information (e.g., user indication of accuracy, reference labels, or other information). In another use case, where machine learning model 302 is a neural network, connection weights may be adjusted to reconcile differences between the neural network's prediction and the reference feedback. In a further use case, one or more neurons (or nodes) of the neural network may require that their respective errors be sent backward through the neural network to them to facilitate the update process (e.g., backpropagation of error). Updates to the connection weights may, for example, be reflective of the magnitude of error propagated backward after a forward pass has been completed. In this way, for example, the machine learning model 302 may be trained to generate better predictions. For example, in some embodiments, inputs 304 may comprise a time of day and reference feedback information 306 (which is fed back as input to the machine learning model 302) may include an amount of power consumed at that specific time or time period. Accordingly, when a time is provided as input 304 to machine learning model 302, machine learning model 302 may provide an output 306 including a predicted amount of power to be consumed at such time or time period. In some embodiments, system 100 may include multiple models that are trained to output different predictions (e.g., the described above or other predictions).

In some embodiments, the electromagnetic emitters 142 may be movable within the enclosed structure 201. For example, the electromagnetic emitters 142 may move along with the movement of the item 202 through the enclosed structure 201. In some embodiments, the speed to of the electromagnetic emitters 142 may correspond to the speed of the belt 204 that moves the item 202 from one end of the enclosed structure 201 to another end of the enclosed structure. In some embodiments, the speed of the belt 204 may be modified based on a size of the item 202. For example, a larger sized item 202 may require more time to be sanitized and disinfected than a smaller sized item 202. Accordingly, in response to a detection of a size of the item 202, the computer system 102 may change the speed at which the belt 204 moves and as such, the speed at which the electromagnetic emitters 142 move may also be changed. This is advantageous because it ensures that the item is properly sanitized or disinfected regardless of the size of the item 202 that travels through the enclosed structure 201.

In some embodiments, in response to obtaining a size of the item 202 or information associated with the size of the item 202, the computer system 102 (e.g., electromagnetic emitter setting subsystem 118) may adjust the intensity of the radiation emitted by the electromagnetic emitters 142. For example, in response to obtaining a size of the item 202 or information associated with the size of the item 202, the computer system 102 (e.g., electromagnetic emitter setting subsystem 118) may adjust the intensity of one or more electromagnetic emitters 142 proximate the location of the item 202, such that the intensity of the electromagnetic emitters 142 is increased for a smaller sized item and decreased for a larger sized item. The intensity of the radiation emitted by the electromagnetic emitters 142 may be inversely proportional to the size of the item 202. In some embodiments, the computer system 102 (e.g., electromagnetic emitter setting subsystem 118) may adjust the intensity of one or more electromagnetic emitters 142 proximate the location of the item 202, such that the intensity of the electromagnetic emitters 142 is decreased for a smaller sized item and increased for a larger sized item. The intensity of the radiation emitted by the electromagnetic emitters 142 may be directly proportional to the size of the item 202. This is advantageous because it reduces the amount of power required to maintain the electromagnetic emitters 142 in an on state and ensures that the item 202 is being properly disinfected or sanitized.

In some embodiments, in response to obtaining a location (or position) of the item 202 on the belt 204, the computer system 102 (e.g., the electromagnetic emitter setting subsystem 118) may adjust the intensity of the radiation emitted by the electromagnetic emitters 142. For example, in response to obtaining a location of the item 202, the computer system 102 (e.g., electromagnetic emitter setting subsystem 118) may adjust the intensity of one or more electromagnetic emitters 142, such that the intensity of the electromagnetic emitters 142 is increased when an item moves away from the electromagnetic emitters 142 and is decreased when an item moves towards the electromagnetic emitters 142. The intensity of the radiation emitted by the electromagnetic emitters 142 may be directly proportional to a distance of the item from the electromagnetic emitters 142. This is advantageous because it reduces the amount of power required to maintain the electromagnetic emitters 142 in an on state and ensures that the item 202 is being properly disinfected or sanitized.

In some embodiments, in response to obtaining a notification that an item 202 has been detected, the computer system 102 (e.g., image sensor setting subsystem 120) may generate a signal to turn on one or more of the image sensors 144. For example, the computer system 102 (e.g., image sensor setting subsystem 120) may generate a signal to turn on (e.g., a first state) one or more image sensors 144 that are proximate to the location of the item 202 on the belt 204, while the other image sensors 144 remain off (e.g., a second state). In other words, based on a detected location of the item 202 (e.g., detected by one or more item sensors 146, which may be arranged throughout the enclosed structure 201) within the enclosed structure 201, the computer system 102 may turn on certain image sensors 144 (such that certain images sensors 144 capture images of, for example, item 202 that is exposed to electromagnetic radiation) that are proximate to the item 202, while maintaining the other image sensors 144 in an off state. This is advantageous because it reduces the amount of power required to maintain the image sensors 144 in an on state. In some embodiments, once the item 202 moves away from the image sensors 144 that were turned on, the computer system 102 (e.g., image sensor setting subsystem 120) may generate a signal to turn off such image sensors 144 in response to a change in the location of the item 202 (e.g., in response to the item 202 being more than a threshold distance from such image sensors 144). In some embodiments, the image sensors 144 may automatically turn off a threshold period of time after they were turned on. The threshold period of time may be dependent on, for example, an amount of power consumed by the physical structure 140, total amount of power consumed by an infrastructure (not shown) that houses the physical structure 140, and/or the time during the day. Alternatively, in response to a detection of an item 202 by the item sensor 146, the computer system 102 may generate a signal to turn on all of the image sensors 144 within the enclosed structure 201. When no item is detected, the image sensors 144 may remain in an off state.

In some embodiments, the computer system 102 may determine a set of image sensors 144 to turn on. Such a set may include every second image sensor 144, every third image sensor 144, etc. Such a determination of a set of image sensors 144 may be based on one or more factors, including, for example, a size of the detected item, amount of power consumed by the physical structure 140, total amount of power consumed by an infrastructure (not shown) that houses the physical structure 140, and/or the time during the day. For example, the computer system 102 may determine or obtain a value of the amount of power consumed by the physical structure 140 (e.g., via an electrical usage monitor) and based on the value of the amount of power consumed by the physical structure 140, the computer system 102 (e.g., image sensor setting subsystem 120) may determine a number of image sensors 144 to turn on in order to capture one or more images associated with the item 202. In some embodiments, the determination of the number of image sensors 144 to turn on (e.g., in response to a detection of an item) may be a multi-tiered determination. For example, if a value of the amount of power consumed by the physical structure 140 is above a first threshold, then the computer system 102 may determine a first number of image sensors 144 to turn on and if a value of the amount of power consumed by the physical structure 140 is above a second threshold, then the computer system 102 may determine a second number of image sensors 144 to turn on. Similar determinations may be made by the computer system 102 based on the obtained or determined value of an amount of power consumed by an infrastructure (not shown) that houses the physical structure 140. In some embodiments, a number of images captured by each image sensor 144 may be determined based on one or more factors, including, for example, a size of the detected item, amount of power consumed by the physical structure 140, total amount of power consumed by an infrastructure (not shown) that houses the physical structure 140, and/or the time during the day.

In some embodiments, the computer system 102 may determine or predict an amount of power consumed at different times during the day and based on such a determination or prediction, may determine a number of image sensors to turn on. For example, the computer system 102 may determine that at 1 pm, the consumption of power is at 50% and at 3 pm, the consumption of power is at 85%. The computer system 102 may determine a number of images sensors 144 to turn on based on a current time and based on such determinations of the consumption of power at different times during the day. In some embodiments, an as described above with regard to FIG. 3, computer system 102 may utilize a machine learning model to facilitate the prediction of an amount of power consumed at a specific time during the day.

In some embodiments, the image sensors 144 may be movable or an angle of the image sensors 144 may be changed within the enclosed structure 201. For example, the image sensors 144 may move along with the movement of the item 202 through the enclosed structure 201 and/or the image sensors 144 may change the angle of view based on the movement of the item through the enclosed structure 201. In some embodiments, the speed to of the image sensors 144 (e.g., speed of movement or speed of changing angle of view) may correspond to the speed of the belt 204 that moves the item 202 from one end of the enclosed structure 201 to another end of the enclosed structure 201.

In some embodiments, in response to obtaining a size of the item 202 or information associated with the size of the item 202, the computer system 102 (e.g., image sensor setting subsystem 120) may adjust the focal length (e.g., zoom level) of the image sensor 144. For example, in response to obtaining a size of the item 202 or information associated with the size of the item 202, the computer system 102 (e.g., image sensor setting subsystem 120) may adjust the focal length of one or more image sensors 144 proximate the location of the item 202, such that the focal length of the image sensors 144 is increased for a smaller sized item and decreased for a larger sized item. The focal length of the image sensors 144 may be inversely proportional to the size of the item 202. Although the above description indicates that the electromagnetic emitters 142 and image sensors 144 are turned on in response to a detection of an item 202, the electromagnetic emitters 142 and image sensors 144 may always remain in on state or may remain in an on state for a specific period of time.

In some embodiments, in response to obtaining a location of the item 202 on the belt 204, the computer system 102 (e.g., the image sensor setting subsystem 120) may adjust the focal length of the image sensors 144. For example, in response to obtaining a location of the item 202, the computer system 102 (e.g., image sensor setting subsystem 120) may adjust the focal length of the image sensors 144, such that the focal length of the image sensors 144 is increased when an item moves away from the image sensor 144 and is decreased when an item moves towards the image sensor 144. The focal length of the image sensor 144 may be directly proportional to a distance of the item from the image sensors 144.

In some embodiments, one or more electromagnetic emitters 142 may expose the item 202 to electromagnetic radiation (e.g., UV light), for example, when the item 202 passes through the enclosed structure 201. Exposure of the item 202 to electromagnetic radiation (e.g., UV light) facilitates sanitizing and disinfecting the item 202. As noted above, in some embodiments, certain electromagnetic emitters 142 may expose the item 202 to electromagnetic radiation (e.g., UV light) based on the proximity of the item 202 to such electromagnetic emitters 142 and the intensity of radiation by such electromagnetic emitters 142 may be based on a size of the item 202. As illustrated in FIG. 2B, in response to exposure to electromagnetic radiation (e.g., UV light), one or more patterns 210 (e.g., affixed to the item 202) may become visible. In other words, one or more patterns 210 (e.g., printed with fluorescent ink) that are affixed to the item 202 may not be visible unless the item or portion of the item is exposed to electromagnetic radiation (e.g., UV light). Alternatively, the pattern 210 may be visible regardless of the exposure of the item 202 to electromagnetic radiation. Although FIG. 2B illustrates one pattern 210, item 202 may be affixed with multiple copies of the same pattern 210 on different portions of the item 202. This is advantageous because item 202 could be positioned in different ways on the belt 204, and by affixing multiple copies of the pattern 210 on the item 202, the image sensors 144 are more likely to recognize such a pattern 210 (especially if a pattern is hidden from a view of one of the image sensors 144). Further, since the pattern 210 may not be visible to the naked eye, item 202 may be more aesthetically pleasing.

In some embodiments, the image sensors 144 may capture one or more images of the item 202 (e.g., when the item 202 is exposed to electromagnetic radiation). As noted above, in some embodiments, certain image sensors 144 may be turned on based on the proximity of the item 202 to such image sensors 144 and the focal length of such image sensors 144 may be determined based on a size of the item 202. As the item 202 travels through the enclosed structure 201, the plurality of image sensors 144 may capture a plurality of images of the item 202, which is exposed to electromagnetic radiation (e.g., UV light). The pattern 210 may correspond to, for example, information to identify the item 202. For example, pattern 210 may correspond to a Quick Response (QR) code or any other barcode and may include encoded information associated with the item 202.

The computer system 102 (e.g., pattern recognition subsystem 112) may obtain the plurality of images associated with the item 202 and may process (e.g., review) the images to identify or recognize the pattern 210 captured by the image sensors 144. For example, based on the obtained images, the computer system 102 (e.g., pattern recognition subsystem 112) may determine a type of pattern that has been captured by the images. In other words, for example, the computer system 102 (e.g., pattern recognition subsystem 112) may determine whether the pattern is a first type (e.g., a QR code), a second type (e.g., a universal product code (UPC)), or another type of barcode. Based on such a determination, the computer system 102 (e.g., information decoding subsystem 114) may identify an algorithm to decode the information associated with the recognized pattern 210. For example, computer system 102 may retrieve an algorithm (e.g., associated with the identified type of pattern) from memory 105 or database 132 in order to decode the information included in the pattern 210.

In some embodiments, although the computer system 102 (e.g., pattern recognition subsystem 112) may obtain a plurality of images associated with item 202, the computer system 102 may stop processing (e.g., reviewing) other images and may discard such other images without processing such other images if the computer system 102 recognizes the pattern included in a previously processed image associated with item 202. In other words, for example, if the computer system 102 obtains five images associated with item 202, and during the processing of the second image, the computer system 102 recognizes the pattern 210, the computer system 102 may stop processing (e.g., reviewing) the other three remaining images and may discard the other three remaining images without processing the other three remaining images. This is advantageous because it reduces the processing burden of the computer system 102 because the computer system 102 may not need to process every single image that it obtains. For example, the computer system 102 may utilize fewer computing resources since the computer system 102 may not need to process every single image that it obtains. This may help the computer system 102 focus its computing resources on other functions to be performed by the computer system 102.

In some embodiments, one or more images (e.g., associated with item 202) obtained by the computer system 102 may only include a portion of the pattern 210. In other words, pattern 210 may be partially hidden from the view of the image sensors 144. Accordingly, the images captured by the image sensors 144 may only include one or more portions of the pattern 210. In such a case, the computer system 102 (e.g., the pattern recognition system) may recognize a first portion of pattern 210 in a first image, a second portion of pattern 210 in a second image, and other portions of the pattern 210 in one or more other images and may process these images (e.g., by merging the images) in order to recognize the pattern 210.

In some embodiments, the computer system 102 (e.g., information decoding subsystem 114) may decode the information included in the pattern 210. As noted above, the pattern 210 may include encoded information, and the computer system 102 may decode the encoded information using a decoding algorithm associated with the recognized pattern 210. In some embodiments, the decoded information may be used to identify the item 202. In other words, the decoded information may include several pieces of information, including information to identify item 202. In some embodiments, the information associated with item 202 may be displayed (e.g., by display subsystem 122) via a display.

Figure 4:
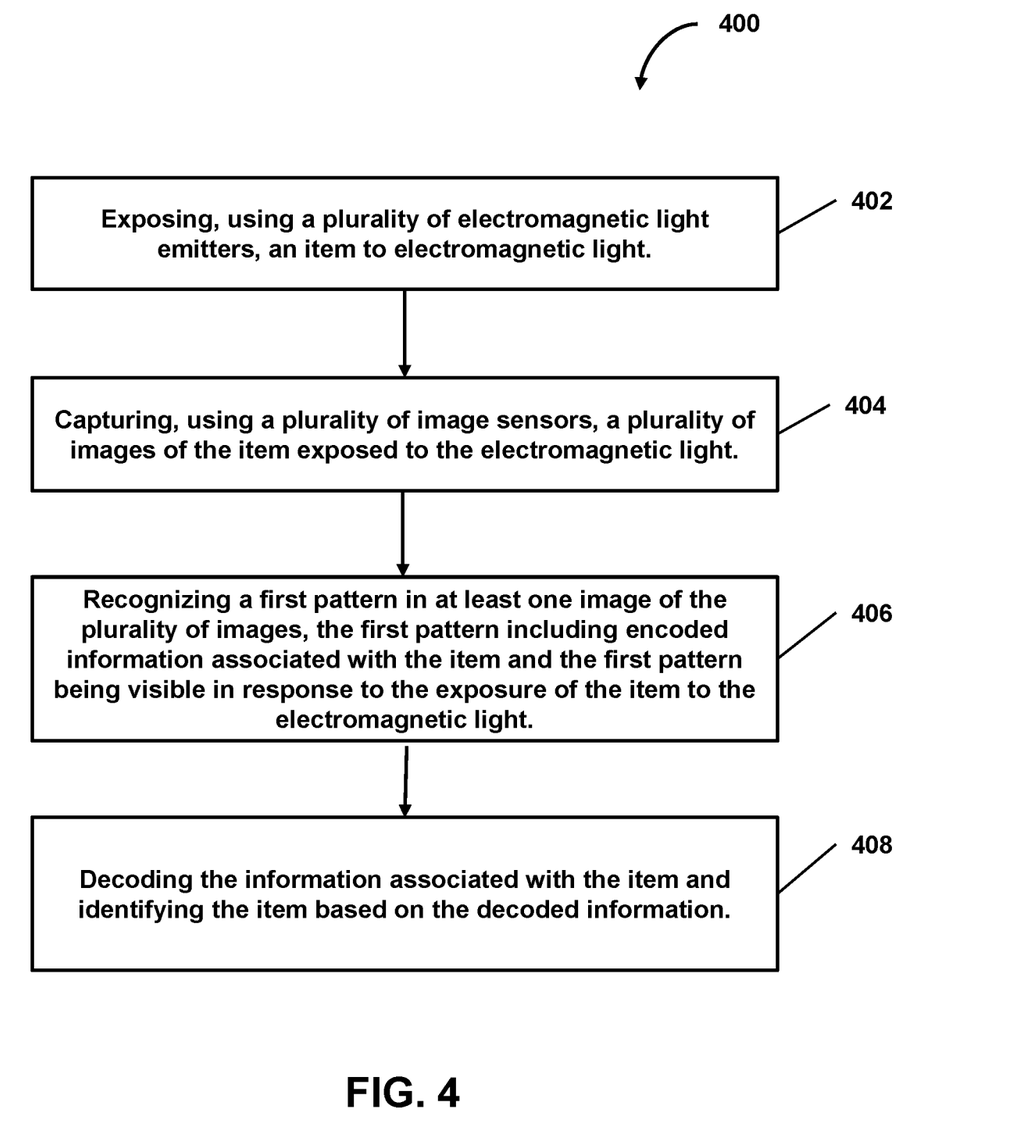
FIG. 4 shows a flowchart of a method for disinfecting and identifying an item, in accordance with one or more embodiments.
Figure 5:
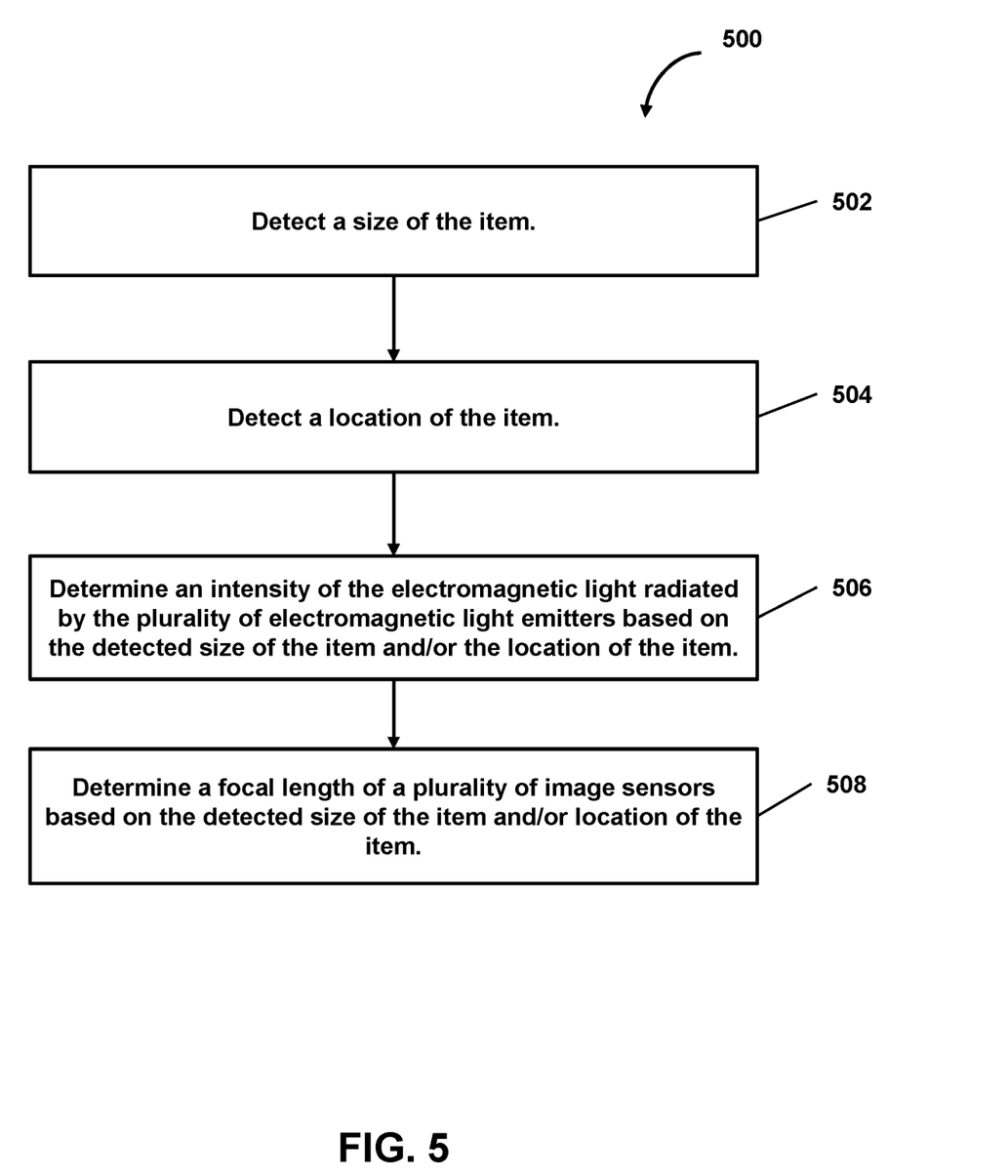
FIG. 5 shows a flowchart of a method for facilitating determination of settings for the plurality of images sensors and the plurality of electromagnetic light emitters, in accordance with one or more embodiments.

FIGS. 4 and 5 are example flowcharts of processing operations of methods that enable the various features and functionality of the system as described in detail above. The processing operations of each method presented below are intended to be illustrative and non-limiting. In some embodiments, for example, the methods may be accomplished with one or more additional operations not described, and/or without one or more of the operations discussed. Additionally, the order in which the processing operations of the methods are illustrated (and described below) is not intended to be limiting.

In some embodiments, the methods may be implemented in one or more processing devices (e.g., a digital processor, an analog processor, a digital circuit designed to process information, an analog circuit designed to process information, a state machine, and/or other mechanisms for electronically processing information). The processing devices may include one or more devices executing some or all of the operations of the methods in response to instructions stored electronically on an electronic storage medium. The processing devices may include one or more devices configured through hardware, firmware, and/or software to be specifically designed for execution of one or more of the operations of the methods.

FIG. 4 shows a method 400 performed for disinfecting and identifying an item. In step 402, an item may be exposed using a plurality of electromagnetic light emitters. The plurality of electromagnetic light emitters may be arranged throughout an enclosed structure such that a first electromagnetic light emitter is arranged at a first location proximate a first opening of the enclosed structure and a second electromagnetic light emitter is arranged at a second location proximate a second opening of the enclosed structure. The electromagnetic light emitters may be UV light emitters. In step 404, a plurality of images of the item may be captured using a plurality of image sensors. The plurality of image sensors may be arranged throughout the enclosed structure. For example, the plurality of image sensors may be interspersed between the plurality of electromagnetic light emitters. A number of the plurality of electromagnetic light emitters to emit electromagnetic light and a number of the plurality of image sensors to capture images may be determined based on one or more factors, including, but not limited to, a current time of the day, a size of the item, amount of power utilized by the enclosed structure, amount of power utilized by an infrastructure that includes the enclosed structure, and/or other factors described in this disclosure. Further, certain electromagnetic light emitters and image sensors (e.g., the one that are determined to be within a threshold distance from the item) may be turned on in response to a detection of an item and such electromagnetic light emitters and image sensors may be turned off in response to the item being equal to or greater than the threshold distance from the electromagnetic light emitters and image sensors.

In step 406, a first pattern in at least one image of the plurality of image may be recognized. The first pattern may include encoded information associated with the item and the first pattern may be visible in response to the exposure of the item to the electromagnetic light. For example, based on the captured images, a type of pattern that has been captured by the images may be determined. In other words, for example, whether the first pattern is a first type (e.g., a QR code), a second type (e.g., a universal product code (UPC)), or another type of barcode may be determined. In step 408, the information associated with the item may be decoded and the item may be identified based on the decoded information. For example, based on recognized type of pattern, an algorithm to decode the encoded information may be identified and such an algorithm may be used to decode the encoded information associated with the first pattern.

FIG. 5 shows a method 500 performed for facilitating determination of settings for the plurality of images sensors and the plurality of electromagnetic light emitters. In step 502, a size of an item may be determined and in step 504, a location (or position) of the item (e.g., within an enclosed structure) may be determined. Such determination may be done based on one or more items (or object) sensors discussed above. In step 506, an intensity of the electromagnetic light radiated by the plurality of electromagnetic light emitters may be determined based on the detected size of the item and/or the location of the item. For example, intensity of one or more electromagnetic emitters may be adjusted such that the intensity of the electromagnetic emitters is increased for a smaller sized item and decreased for a larger sized item. The intensity of the radiation emitted by the electromagnetic emitters may be inversely proportional to the size of the item 202. Alternatively, intensity of one or more electromagnetic emitters may be adjusted such that the intensity of the electromagnetic emitters is decreased for a smaller sized item and increased for a larger sized item. The intensity of the radiation emitted by the electromagnetic emitters may be directly proportional to the size of the item. Further, the intensity of one or more electromagnetic emitters may be adjusted such that the intensity of the electromagnetic emitters is increased when an item moves away from the electromagnetic emitters and is decreased when an item moves towards the electromagnetic emitters. The intensity of the radiation emitted by the electromagnetic emitters may be directly proportional to a distance of the item from the electromagnetic emitters.

In step 508, a focal length of a plurality of image sensors may be determined based on a detected size of the item and/or location of the item. The focal length of one or more image sensors may be adjusted such that the focal length of the image sensors is increased for a smaller sized item and decreased for a larger sized item. The focal length of the image sensors may be inversely proportional to the size of the item. Further, the focal length of the image sensors may be adjusted such that the focal length of the image sensors is increased when an item moves away from the image sensor and is decreased when an item moves towards the image sensor. The focal length of the image sensor may be directly proportional to a distance of the item from the image sensors.

In some embodiments, the various computers and subsystems illustrated in FIG. 1 may include one or more computing devices that are programmed to perform the functions described herein. The computing devices may include one or more electronic storages (e.g., memory 105, database(s) 132, or other electronic storages), one or more physical processors programmed with one or more computer program instructions, circuitry, and/or other components. The computing devices may include communication lines or ports to enable the exchange of information within a network (e.g., network 152) or other computing platforms via wired or wireless techniques (e.g., Ethernet, fiber optics, coaxial cable, Wi-Fi, Bluetooth, near field communication, or other technologies). The computing devices may include a plurality of hardware, software, and/or firmware components operating together. For example, the computing devices may be implemented by a cloud of computing platforms operating together as the computing devices.

The electronic storages may include non-transitory storage media that electronically stores information. The storage media of the electronic storages may include one or both of (i) system storage that is provided integrally (e.g., substantially non-removable) with servers or client devices or (ii) removable storage that is removably connectable to the servers or client devices via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storage may store software algorithms, information determined by the processors, information obtained from servers, information obtained from client devices, or other information that enables the functionality as described herein.

The processors may be programmed to provide information processing capabilities in the computing devices. As such, the processors may include one or more of a digital processor, an analog processor, a digital circuit designed to process information, an analog circuit designed to process information, a state machine, and/or other mechanisms for electronically processing information. In some embodiments, the processors may include a plurality of processing units. These processing units may be physically located within the same device, or the processors may represent processing functionality of a plurality of devices operating in coordination. The processors may be programmed to execute computer program instructions to perform functions described herein of subsystems 112-122 or other subsystems. The processors may be programmed to execute computer program instructions by software; hardware; firmware; some combination of software, hardware, or firmware; and/or other mechanisms for configuring processing capabilities on the processors.

It should be appreciated that the description of the functionality provided by the different subsystems 112-122 described herein is for illustrative purposes, and is not intended to be limiting, as any of subsystems 112-122 may provide more or less functionality than is described. For example, one or more of subsystems 112-122 may be eliminated, and some or all of its functionality may be provided by other ones of subsystems 112-122. As another example, additional subsystems may be programmed to perform some or all of the functionality attributed herein to one of subsystems 112-122.

Although the present disclosure has been described in detail for the purpose of illustration based on what is currently considered to be the most practical and preferred embodiments, it is to be understood that such detail is solely for that purpose and that the disclosure is not limited to the disclosed embodiments, but, on the contrary, is intended to cover modifications and equivalent arrangements that are within the scope of the appended claims. For example, it is to be understood that the present disclosure contemplates that, to the extent possible, one or more features of any embodiment can be combined with one or more features of any other embodiment.

The present techniques will be better understood with reference to the following enumerated embodiments:

1. A method comprising: exposing, using a plurality of electromagnetic light emitters, an item to electromagnetic light; capturing, using a plurality of image sensors, a plurality of images of the item exposed to the electromagnetic light; recognizing a first pattern in at least one image of the plurality of images, the first pattern including encoded information associated with the item and the first pattern being visible in response to the exposure of the item to the electromagnetic light; decoding the information associated with the item; and identifying the item based on the decoded information.

2. The method of embodiment 1, wherein the plurality of electromagnetic light emitters are arranged throughout an enclosed structure such that a first electromagnetic light emitter is arranged at a first location proximate a first opening of the enclosed structure and a second electromagnetic light emitter is arranged at a second location proximate a second opening of the enclosed structure.

3. The method of any of embodiments 1-2, wherein the plurality of image sensors are arranged throughout the enclosed structure.

4. The method of any of embodiments 1-3, wherein the plurality of cameras are arranged throughout the tunnel structure in between the plurality of UV light emitters such that at least one camera is arranged between the first location and the second location of the tunnel structure.

5. The method of any of embodiments 1-4, further comprising: detecting, using a sensor, the item, the sensor being arranged proximate the first opening of the enclosed structure; and in response to a detection of the item, causing at least the first electromagnetic light emitter and a first image sensor proximate the first opening to turn on.

6. The method of any of embodiments 1-5, wherein recognizing the first pattern includes: recognizing a first portion of a pattern in a first image of the plurality of images and recognizing a second portion of the pattern in a second image of the plurality of images; and merging the first portion and the second portion to recognize the first pattern.

7. The method of any of embodiments 1-6, wherein recognizing the first pattern includes: recognizing the first pattern in a first image of the plurality of images; and discarding one or more other images of the plurality of images in response to the recognition of the first pattern in the first image.

8. The method of any of embodiments 1-7, further comprising: detecting a size of the item; and determining an intensity of the electromagnetic light radiated by the plurality of electromagnetic light emitters based on the detected size of the item.

9. The method of any of embodiments 1-8, further comprising: detecting a size of the item; and determining a focal length of the plurality of image sensors based on the detected size of the item.

10. The method of any of embodiments 1-9, further comprising: detecting a location of the item; and determining an intensity of the electromagnetic light radiated by the plurality of electromagnetic light emitters based on the detected location of the item.

11. The method of any of embodiments 1-10, further comprising: detecting a location of the item; and determining a focal length of the plurality of image sensors based on the detected location of the item.

12. A tangible, non-transitory, computer-readable medium storing instructions that, when executed by a data processing apparatus, cause the data processing apparatus to perform operations comprising those of any of embodiments 1-11.

13. A system comprising: one or more processors; and memory storing instructions that, when executed by the processors, cause the processors to effectuate operations comprising those of any of embodiments 1-11.

14. A system comprising: circuitry to effectuate operations comprising those of any of embodiments 1-11.

What is claimed is:

1. A system comprising:
electromagnetic light emitters configured to expose an item to electromagnetic light, wherein the electromagnetic light emitters are arranged throughout an enclosed structure such that a first electromagnetic light emitter is arranged at a first location proximate a first opening of the enclosed structure and a second electromagnetic light emitter is arranged at a second location proximate a second opening of the enclosed structure;
image sensors configured to capture images of the item exposed to the electromagnetic light, wherein the image sensors are arranged throughout the enclosed structure; and circuitry configured to:
  recognizing a first pattern in at least one image of the images, the first pattern including encoded information associated with the item and the first pattern being visible in response to the exposure of the item to the electromagnetic light; and
  decoding the encoded information associated with the item.

2. The system of claim 1, further comprising:
a sensor configured to detect the item, the sensor being arranged proximate the first opening of the enclosed structure,
wherein the circuitry is configured to:
  in response to a detection of the item, causing at least the first electromagnetic light emitter and a first image sensor proximate the first opening to turn on.

3. The system of claim 1, wherein recognizing the first pattern includes:
recognizing a first portion of a pattern in a first image of the images and recognizing a second portion of the pattern in a second image of the images; and
merging the first portion and the second portion to recognize the first pattern.

4. The system of claim 1, wherein recognizing the first pattern includes:
recognizing the first pattern in a first image of the images; and
discarding one or more other images of the images in response to the recognition of the first pattern in the first image.

5. The system of claim 1, wherein the circuitry is configured to:
detect a size of the item; and
adjust, based on the detected size of the item, an intensity of the electromagnetic light radiated by one or more electromagnetic light emitters of the electromagnetic light emitters.

6. The system of claim 1, wherein the circuitry is configured to:
detect a size of the item; and
adjust a focal length of the image sensors based on the detected size of the item.

7. The system of claim 1, wherein the circuitry is configured to:
detect a location of the item; and
adjust, based on the detected location of the item, an intensity of the electromagnetic light radiated by one or more electromagnetic light emitters of the electromagnetic light emitters.

8. The system of claim 1, wherein the circuitry is configured to:
detect a location of the item; and
adjust a focal length of the image sensors based on the detected location of the item.

9. The system of claim 1, wherein the electromagnetic light emitters comprise one or more electromagnetic light emitters configured to move at least within the enclosed structure to expose the item to the electromagnetic light radiated by the one or more electromagnetic light emitters,
wherein the circuitry is configured to:
  detect a size of the item; and
  adjust, based on the detected size of the item, a speed at which the one or more electromagnetic light emitters move to expose the item to the electromagnetic light radiated by the one or more electromagnetic light emitters.

10. The system of claim 1, further comprising:
an item transport surface on which the item is placed and configured to move the item through the enclosed structure;
wherein the circuitry is configured to:
  detect a size of the item; and
  adjust, based on the detected size of the item, a speed at which the item transport surface moves the item through the enclosed structure.

11. An ultraviolet (UV) disinfection and identification system, the system comprising:
a tunnel structure comprising a first opening and a second opening;
a plurality of ultraviolet (UV) light emitters configured to expose an item to UV light, wherein the plurality of UV light emitters are arranged throughout the tunnel structure such that a first UV light emitter is arranged at a first location proximate the first opening and a second UV light emitter is arranged at a second location proximate the second opening;
a plurality of cameras configured to capture a plurality of images of the item exposed to the UV light, wherein the plurality of cameras are arranged throughout the tunnel structure in between the plurality of UV light emitters such that at least one camera is arranged between the first location and the second location of the tunnel structure; and
circuitry configured to:
  recognize a first pattern in at least one image of the plurality of images, the first pattern including encoded information associated with the item and the first pattern being visible in response to the exposure of the item to the UV light;
  decode the encoded information associated with the item; and
  identify the item based on the decoded information.

12. The UV disinfection and identification system of claim 11, further comprising:
a sensor configured to detect the item, the sensor being arranged proximate the first opening of the tunnel structure,
wherein the circuitry is configured to:
  in response to a detection of the item, cause at least the first UV light emitter and a first camera proximate the first opening to turn on.

13. The UV disinfection and identification system of claim 11, wherein recognizing the first pattern includes:
recognizing a first portion of a pattern in a first image of the plurality of images and recognizing a second portion of the pattern in a second image of the plurality of images; and
merging the first portion and the second portion to recognize the first pattern.

14. The UV disinfection and identification system of claim 11, wherein recognizing the first pattern includes:
recognizing the first pattern in a first image of the plurality of images; and
discarding one or more other images of the plurality of images in response to the recognition of the first pattern in the first image.

15. The UV disinfection and identification system of claim 11, wherein the circuitry is configured to:
detect a size of the item; and
adjust, based on the detected size of the item, an intensity of the UV light radiated by one or more UV light emitters of the plurality of UV light emitters such that:
  the intensity of the UV light is a first intensity in response to the detected size being a first size; and the intensity of the UV light is a second intensity different from the first intensity in response to the detected size being a second size different from the first size.

16. The UV disinfection and identification system of claim 11, wherein the circuitry is configured to:
   detect a location of the item; and
   adjust, based on the detected location of the item, an intensity of the UV light radiated by one or more UV light emitters of the plurality of UV light emitters such that:
      the intensity of the UV light is a first intensity in response to the detected location of the item being a first location; and
      the intensity of the UV light is a second intensity different from the first intensity in response to the detected location of the item being a second location different from the first location.

17. The UV disinfection and identification system of claim 11, wherein the circuitry is configured to:
   detect a size or a location of the item; and
   adjust, based on the detected size or location of the item, a focal length of one or more cameras of the plurality of cameras.

18. The UV disinfection and identification system of claim 11, wherein the plurality of UV light emitters comprise one or more UV light emitters configured to move at least within the tunnel structure to expose the item to the UV light radiated by the one or more UV light emitters, wherein the circuitry is configured to:
   detect a size of the item; and
   adjust, based on the detected size of the item, a speed at which the one or more UV light emitters move to expose the item to the UV light radiated by the one or more UV light emitters such that:
      the adjusted speed is a first speed in response to the detected size of the item being a first size; and
      the adjusted speed is a second speed different from the first speed in response to the detected size of the item being a second size different from the first size.

19. The UV disinfection and identification system of claim 11, further comprising:
   a belt on which the item is placed and configured to move the item through the tunnel structure;
   wherein the circuitry is configured to:
      detect a size of the item; and
      adjust, based on the detected size of the item, a speed at which the belt moves the item through the tunnel structure such that:
         the adjusted speed is a first speed in response to the detected size of the item being a first size; and
         the adjusted speed is a second speed different from the first speed in response to the detected size of the item being a second size different from the first size.

* * * * *